United States Patent
Cherpeck et al.

[11] Patent Number: 5,749,929
[45] Date of Patent: May 12, 1998

[54] FUEL ADDITIVE COMPOSITIONS CONTAINING AROMATIC ESTERS OF POLYALKYLPHENOXYALKANOLS AND POLY (OXYALKYLENE) AMINES

[75] Inventors: Richard E. Cherpeck, Cotati; Jack E. Morris, El Cerrito; Majid R. Ahmadi, Pinole, all of Calif.

[73] Assignee: Chevron Chemical Company, San Ramon, Calif.

[21] Appl. No.: 833,463

[22] Filed: Apr. 7, 1997

Related U.S. Application Data

[63] Continuation-in-part of Ser. No. 647,486, May 14, 1996, Pat. No. 5,618,320.

[51] Int. Cl.$^6$ ............................ C10L 1/22; C10L 1/18
[52] U.S. Cl. .................... 44/387; 44/399; 44/400; 44/433
[58] Field of Search .................. 44/387, 399, 400, 44/433

[56] References Cited

U.S. PATENT DOCUMENTS

| | | | |
|---|---|---|---|
| 2,714,607 | 8/1955 | Matter | 260/471 |
| 3,149,933 | 9/1964 | Ley et al. | 44/75 |
| 3,285,855 | 11/1966 | Dexter et al. | 252/57 |
| 3,330,859 | 7/1967 | Dexter et al. | 260/473 |
| 3,434,814 | 3/1969 | Dubeck et al. | 44/69 |
| 3,849,085 | 11/1974 | Kreuz et al. | 44/78 |
| 4,134,846 | 1/1979 | Machleder et al. | 252/51.5 A |
| 4,191,537 | 3/1980 | Lewis et al. | 44/71 |
| 4,247,301 | 1/1981 | Honnen | 44/63 |
| 4,320,021 | 3/1982 | Lange | 252/51.5 R |
| 4,328,322 | 5/1982 | Baron | 521/163 |
| 4,347,148 | 8/1982 | Davis | 252/51.5 R |
| 4,386,939 | 6/1983 | Lange | 44/63 |
| 4,859,210 | 8/1989 | Franz et al. | 44/53 |
| 5,090,914 | 2/1992 | Reardan et al. | 435/188 |
| 5,112,364 | 5/1992 | Rath et al. | 44/418 |
| 5,196,142 | 3/1993 | Mollet et al. | 252/311 |
| 5,196,565 | 3/1993 | Ross | 560/55 |
| 5,211,721 | 5/1993 | Sung et al. | 44/389 |
| 5,380,345 | 1/1995 | Cherpeck | 44/399 |
| 5,407,452 | 4/1995 | Cherpeck | 44/399 |
| 5,427,591 | 6/1995 | Cherpeck | 44/400 |
| 5,618,320 | 4/1997 | Cherpeck | 44/399 |

FOREIGN PATENT DOCUMENTS

| | | | |
|---|---|---|---|
| WO94/14926 | 7/1994 | WIPO | C10L 1/18 |
| WO95/04118 | 2/1995 | WIPO | C10L 1/18 |
| WO95/11955 | 5/1995 | WIPO | C10L 1/18 |
| WO95/15366 | 6/1995 | WIPO | C10L 1/18 |

*Primary Examiner*—Jerry D. Johnson
*Attorney, Agent, or Firm*—Claude J. Caroli

[57] ABSTRACT

A fuel additive composition comprising: (a) an aromatic ester compound of the formula:

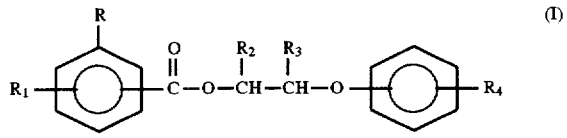

or a fuel soluble salt thereof, wherein R is hydroxy, nitro or $-(CH_2)_x-NR_5R_6$, wherein $R_5$ and $R_6$ are independently hydrogen or lower alkyl having 1 to 6 carbon atoms and x is 0 or 1;

$R_1$, is hydrogen, hydroxy, nitro or $-NR_7R_8$, wherein $R_7$ and $R_8$ are independently hydrogen or lower alkyl having 1 to 6 carbon atoms;

$R_2$ and $R_3$ are independently hydrogen or lower alkyl having 1 to 6 carbon atoms; and $R_4$ is a polyalkyl group having an average molecular weight in the range of about 450 to 5,000; and (b) a poly(oxyalkylene) amine having at least one basic nitrogen atom and a sufficient number of oxyalkylene units to render the poly(oxyalkylene) amine soluble in hydrocarbons boiling in the gasoline or diesel fuel range.

The fuel additive compositions of this invention are useful as fuel additives for the prevention and control of engine deposits.

85 Claims, No Drawings

FUEL ADDITIVE COMPOSITIONS CONTAINING AROMATIC ESTERS OF POLYALKYLPHENOXYALKANOLS AND POLY (OXYALKYLENE) AMINES

This application is a continuation-in-part of application Ser. No. 08/647,486, filed May 14,1996, now U.S. Pat. No. 5,618,320.

BACKGROUND OF THE INVENTION

1. Field of the Invention

This invention relates to fuel additive compositions containing aromatic esters of polyalkylphenoxyalkanols and poly(oxyalkylene) amines. In a further aspect, this invention relates to the use of these additive compositions in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

Similarly, U.S. Pat. No. 3,149,933, issued Sep. 22, 1964 to K. Ley et al., discloses hydrocarbon-substituted amino phenols as stabilizers for liquid fuels.

U.S. Pat. No. 4,386,939, issued Jun. 7, 1983 to R. M. Lange, discloses nitrogen-containing compositions prepared by reacting an amino phenol with at least one 3- or 4-membered ring heterocyclic compound in which the hetero atom is a single oxygen, sulfur or nitrogen atom, such as ethylene oxide. The nitrogen-containing compositions of this patent are taught to be useful as additives for lubricants and fuels.

Nitro phenols have also been employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants and demulsifiers for lubricating oil and fuel compositions.

Similarly, U.S. Pat. No. 3,434,814, issued Mar. 25, 1969 to M. Dubeck et al., discloses a liquid hydrocarbon fuel composition containing a major quantity of a liquid hydrocarbon of the gasoline boiling range and a minor amount sufficient to reduce exhaust emissions and engine deposits of an aromatic nitro compound having an alkyl, aryl, aralkyl, alkanoyloxy, alkoxy, hydroxy or halogen substituent.

More recently, certain poly(oxyalkylene) esters have been shown to reduce engine deposits when used in fuel compositions. U.S. Pat. No. 5,211,721, issued May 18, 1993 to R. L. Sung et al., for example, discloses an oil soluble polyether additive comprising the reaction product of a polyether polyol with an acid represented by the formula RCOOH in which R is a hydrocarbyl radical having 6 to 27 carbon atoms. The poly(oxyalkylene) ester compounds of this patent are taught to be useful for inhibiting carbonaceous deposit formation, motor fuel hazing, and as ORI inhibitors when employed as soluble additives in motor fuel compositions.

Poly(oxyalkylene) esters of amino- and nitrobenzoic acids are also known in the art. For example, U.S. Pat. No. 2,714,607, issued Aug. 2, 1955 to M. Matter, discloses polyethoxy esters of aminobenzoic acids, nitrobenzoic acids and other isocyclic acids. These polyethoxy esters are taught to have excellent pharmacological properties and to be useful as anesthetics, spasmolytics, analeptics and bacteriostatics.

Similarly, U.S. Pat. No. 5,090,914, issued Feb. 25, 1992 to D. T. Reardan et al., discloses poly(oxyalkylene) aromatic compounds having an amino or hydrazinocarbonyl substituent on the aromatic moiety and an ester, amide, carbamate, urea or ether linking group between the aromatic moiety and the poly(oxyalkylene) moiety. These compounds are taught to be useful for modifying macromolecular species such as proteins and enzymes.

U.S. Pat. No. 4,328,322, issued Sep. 22, 1980 to R. C. Baron, discloses amino- and nitrobenzoate esters of oligomeric polyols, such as poly(ethylene) glycol. These materials are used in the production of synthetic polymers by reaction with a polyisocyanate.

U.S. Pat. No. 4,859,210, issued Aug. 22, 1989 to Franz et al., discloses fuel compositions containing (1) one or more polybutyl or polyisobutyl alcohols wherein the polybutyl or polyisobutyl group has a number average molecular weight of 324 to 3,000, or (2) a poly(alkoxylate) of the polybutyl or polyisobutyl alcohol, or (3) a carboxylate ester of the polybutyl or polyisobutyl alcohol. This patent further teaches that when the fuel composition contains an ester of a polybutyl or polyisobutyl alcohol, the ester-forming acid group may be derived from saturated or unsaturated, aliphatic or aromatic, acyclic or cyclic mono- or polycarboxylic acids.

U.S. Pat. Nos. 3,285,855, and 3,330,859 issued Nov. 15, 1966 and Jul. 11, 1967 respectively, to Dexter et al., disclose alkyl esters of dialkyl hydroxybenzoic and hydroxyphenylalkanoic acids wherein the ester moiety contains from 6 to 30 carbon atoms. These patents teach that such esters are useful for stabilizing polypropylene and other organic material normally subject to oxidative deterioration. Similar alkyl esters containing hindered dialkyl hydroxyphenyl groups are disclosed in U.S. Pat. No. 5,196,565, which issued Mar. 23, 1993 to Ross.

U.S. Pat. No. 5,196,142, issued Mar. 23, 1993 to Mollet et al., discloses alkyl esters of hydroxyphenyl carboxylic acids wherein the ester moiety may contain up to 23 carbon atoms. This patent teaches that such compounds are useful as antioxidants for stabilizing emulsion-polymerized polymers.

Commonly assigned U.S. Pat. No. 5,407,452, issued Apr. 18, 1995, and corresponding International Application Publication No. WO 95/04118, published Feb. 9, 1995, disclose certain poly(oxyalkylene) nitro and aminoaromatic esters having from 5 to 100 oxyalkylene units and teach the use of such compounds as fuel additives for the prevention and control of engine deposits.

Similarly, commonly assigned U.S. Pat. No. 5,427,591, issued Jun. 27, 1995, and corresponding International Application Publication No. WO 94/14926, published Jul. 7, 1994, disclose certain poly(oxyalkylene) hydroxyaromatic esters which are useful as fuel additives to control engine deposits.

In addition, commonly assigned U.S. Pat. No. 5,380,345, issued Jan. 10, 1995, and corresponding International Application Publication No. WO 95/15366, published Jun. 8, 1995, disclose certain polyalkyl nitro and aminoaromatic esters useful as deposit control additives for fuels. Moreover, commonly assigned International Application Publication No. WO 95/11955, published May 4, 1995, certain polyalkyl hydroxyaromatic esters which are also useful as deposit control fuel additives.

Poly(oxyalkylene) amines are also well known in the art as fuel additives for the prevention and control of engine deposits. For example, U.S. Pat. No. 4,191,537, issued Mar. 4, 1980 to R. A. Lewis et al., discloses a fuel composition comprising a major portion of hydrocarbons boiling in the gasoline range and from 30 to 2000 ppm of a hydrocarbyl poly(oxyalkylene) aminocarbamate having a molecular weight from about 600 to 10,000, and at least one basic nitrogen atom. The hydrocarbyl poly(oxyalkylene) moiety is composed of oxyalkylene units selected from 2 to 5 carbon oxyalkylene units. These fuel compositions are taught to maintain the cleanliness of intake systems without contributing to combustion chamber deposits.

U.S. Pat. No. 5,112,364, issued May 12, 1992 to Rath et al., discloses gasoline-engine fuels which contain small amounts of a polyetheramine and/or a polyetheramine derivative, wherein the polyetheramine is prepared by reductive amination of a phenol-initiated or alkylphenol-initiated polyether alcohol with ammonia or a primary amine.

U.S. Pat. No. 4,247,301, issued Jan. 27, 1981 to Honnen, discloses hydrocarbyl-substituted poly(oxyalkylene) polyamines, wherein the hydrocarbyl group contains from 1 to 30 carbon atoms and the polyamine moiety contains from 2 to 12 amine nitrogen atoms and from 2 to 40 carbon atoms. This patent teaches that the additives may be prepared by the reaction of a suitable hydrocarbyl-terminated polyether alcohol with a halogenating agent, such as HCl or thionyl chloride, to form a polyether chloride, followed by reaction of the polyether chloride with a polyamine to form the desired poly(oxyalkylene) polyamine. This patent also teaches at Example 6 that the polyether chloride may be reacted with ammonia or dimethylamine to form the corresponding polyether amine or polyether dimethylamine.

Furthermore, commonly assigned copending U.S. patent application Ser. No. 08/647,486, filed May 14, 1996, discloses aromatic esters of polyalkylphenoxyalkanols and their use in fuel compositions for the prevention and control of engine deposits.

SUMMARY OF THE INVENTION

It has now been discovered that the combination of certain aromatic esters of polyalkylphenoxyalkanols with poly(oxyalkylene) amines affords a unique fuel additive composition which provides excellent control of engine deposits, especially intake valve and combustion chamber deposits.

Accordingly, the present invention provides a novel fuel additive composition comprising:

(a) an aromatic ester compound having the following formula or a fuel soluble salt thereof:

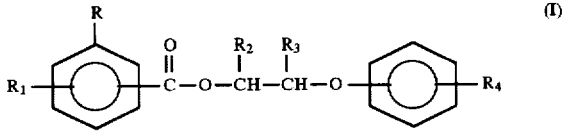

wherein R is hydroxy, nitro or —$(CH_2)_x$—$NR_5R_6$, wherein $R_5$ and $R_6$ are independently hydrogen or lower alkyl having 1 to 6 carbon atoms and x is 0 or 1;

$R_1$ is hydrogen, hydroxy, nitro or —$NR_7R_8$, wherein $R_7$ and $R_8$ are independently hydrogen or lower alkyl having 1 to 6 carbon atoms;

$R_2$ and $R_3$ are independently hydrogen or lower alkyl having 1 to 6 carbon atoms; and $R_4$ is a polyalkyl group having an average molecular weight in the range of about 450 to 5,000; and (b) a poly(oxyalkylene) amine having at least one basic nitrogen atom and a sufficient number of oxyalkylene units to render the poly(oxyalkylene) amine soluble in hydrocarbons boiling in the gasoline or diesel fuel range.

The present invention further provides a fuel composition comprising a major amount of hydrocarbons boiling in the gasoline or diesel range and an effective deposit-controlling amount of a compound of the present invention.

The present invention additionally provides a fuel concentrate comprising an inert stable oleophilic organic solvent boiling in the range of from about 150° F. to 400° F. and from about 10 to 70 weight percent of a compound of the present invention.

Among other factors, the present invention is based on the surprising discovery that the unique combination of certain aromatic esters of polyalkylphenoxyalkanols with poly(oxyalkylene) amines provides excellent control of engine deposits, especially on intake valves and in combustion chambers, when employed as additives in fuel compositions.

DETAILED DESCRIPTION OF THE INVENTION

The Aromatic Ester of Polyalkylphenoxyalkanols

The aromatic ester component of the present additive composition is an aromatic ester of a polyalkylphenoxyalkanol and has the following general formula:

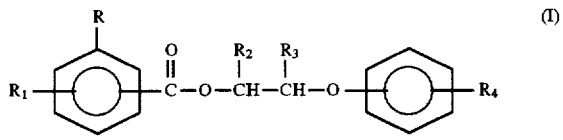
(I)

or a fuel-soluble salt thereof, wherein R, $R_1$, $R_2$, $R_3$ and $R_4$ are as defined hereinabove.

Based on performance (e.g. deposit control), handling properties and performance/cost effectiveness, the preferred aromatics ester compounds employed in the present invention are those wherein R is nitro, amino, N-alkylamino, or —$H_2NH_2$ (aminomethyl). More preferably, R is a nitro, amino or —$H_2NH_2$ group. Most preferably, R is an amino or —$CH_2NH_2$ group, especially amino. Preferably, $R_1$ is hydrogen, hydroxy, nitro or amino. More preferably, $R_1$ is hydrogen or hydroxy. Most preferably, $R_1$ is hydrogen. Preferably, $R_4$ is a polyalkyl group having an average molecular weight in the range of about 500 to 3,000, more preferably about 700 to 3,000, and most preferably about 900 to 2,500. Preferably, the compound has a combination of preferred substituents.

Preferably, one of $R_2$ and $R_3$ is hydrogen or lower alkyl of 1 to 4 carbon atoms, and the other is hydrogen. More preferably, one of $R_2$ and $R_3$ is hydrogen, methyl or ethyl, and the other is hydrogen. Most preferably, $R_2$ is hydrogen, methyl or ethyl, and $R_3$ is hydrogen.

When R and/or $R_1$ is an N-alkylamino group, the alkyl group of the N-alkylamino moiety preferably contains 1 to 4 carbon atoms. More preferably, the N-alkylamino is N-methylamino or N-ethylamino.

Similarly, when R and/or $R_1$ is an N,N-dialkylamino group, each alkyl group of the N,N-dialkylamino moiety preferably contains 1 to 4 carbon atoms. More preferably, each alkyl group is either methyl or ethyl. For example, particularly preferred N,N-dialkylamino groups are N,N-dimethylamino, N-ethyl-N-methylamino and N,N-diethylamino groups.

A further preferred group of compounds are those wherein R is amino, nitro, or —$CH_2NH_2$ and $R_1$ is hydrogen or hydroxy. A particularly preferred group of compounds are those wherein R is amino, $R_1$, $R_2$ and $R_3$ are hydrogen, and $R_4$ is a polyalkyl group derived from polyisobutene.

It is preferred that the R substituent is located at the meta or, more preferably, the para position of the benzoic acid moiety, i.e., para or meta relative to the carbonyloxy group. When $R_1$ is a substituent other than hydrogen, it is particularly preferred that this $R_1$ group be in a meta or para position relative to the carbonyloxy group and in an ortho position relative to the R substituent. Further, in general, when $R_1$ is other than hydrogen, it is preferred that one of R or $R_1$ is located para to the carbonyloxy group and the other is located meta to the carbonyloxy group. Similarly, it is preferred that the $R_4$ substituent on the other phenyl ring is located para or meta, more preferably para, relative to the ether linking group.

The compounds employed in the present invention will generally have a sufficient molecular weight so as to be non-volatile at normal engine intake valve operating temperatures (about 200°–250° C.). Typically, the molecular weight of the compounds employed in this invention will range from about 700 to about 3,500, preferably from about 700 to about 2,500.

Fuel-soluble salts of the compounds of formula I can be readily prepared for those compounds containing an amino or substituted amino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

When the R or $R_1$ substituent is a hydroxy group, suitable salts can be obtained by deprotonation of the hydroxy group with a base. Such salts include salts of alkali metals, alkaline earth metals, ammonium and substituted ammonium salts. Preferred salts of hydroxy-substituted compounds include alkali metal, alkaline earth metal and substituted ammonium salts.

Definitions

As used herein, the following terms have the following meanings unless expressly stated to the contrary.

The term "amino" refers to the group: —$NH_2$.

The term "N-alkylamino" refers to the group: —$NHR_a$ wherein $R_a$ is an alkyl group. The term "N,N-dialkylamino" refers to the group:—$NR_bR_c$, wherein $R_b$ and $R_c$ are alkyl groups.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "polyalkyl" refers to an alkyl group which is generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The term "fuel" or "hydrocarbon fuel" refers to normally liquid hydrocarbons having boiling points in the range of gasoline and diesel fuels.

General Synthetic Procedures

The polyalkylphenoxyalkyl aromatic esters employed in this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Those skilled in the art will also recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

In the present synthetic procedures, a hydroxyl group will preferably be protected, when necessary, as the benzyl or tert-butyldimethylsilyl ether. Introduction and removal of these protecting groups is well described in the art. Amino groups may also require protection and this may be accomplished by employing a standard amino protecting group, such as a benzyloxycarbonyl or a trifluoroacetyl group. Additionally, as will be discussed in further detail hereinbelow, the aromatic esters employed in this invention having an amino group on the aromatic moiety will generally be prepared from the corresponding nitro derivative. accordingly, in many of the following procedures, a nitro group will serve as a protecting group for the amino moiety.

Moreover, the aromatic ester compounds employed in this invention having a —$CH_2NH_2$ group on the aromatic moiety will generally be prepared from the corresponding cyano derivative, —CN. Thus, in many of the following procedures, a cyano group will serve as a protecting group for the —$CH_2NH_2$ moiety.

Synthesis

The polyalkylphenoxyalkyl aromatic esters employed in the present invention may be prepared by a process which initially involves hydroxyalkylation of a polyalkylphenol of the formula:

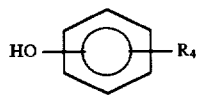
(II)

wherein $R_4$ is as defined herein, with an alkylene carbonate of the formula:

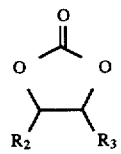
(III)

wherein $R_2$ and $R_3$ are as defined herein, in the presence of a catalytic amount of an alkali metal hydride or hydroxide, or alkali metal salt, to provide a polyalkylphenoxyalkanol of the formula:

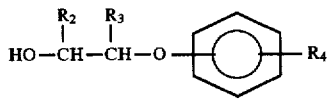
(IV)

wherein $R_2$, $R_3$ and $R_4$ are as defined herein.

The polyalkylphenols of formula II are well known materials and are typically prepared by the alkylation of phenol with the desired polyolefin or chlorinated polyolefin. A further discussion of polyalkylphenols can be found, for example, in U.S. Pat. No. 4,744,921 and U.S. Pat. No. 5,300,701.

Accordingly, the polyalkylphenols of formula II may be prepared from the corresponding olefins by conventional procedures. For example, the polyalkylphenols of formula II above may be prepared by reacting the appropriate olefin or olefin mixture with phenol in the presence of an alkylating catalyst at a temperature of from about 25° C. to 150° C., and preferably 30° C. to 100° C. either neat or in an essentially inert solvent at atmospheric pressure. A preferred alkylating catalyst is boron trifluoride. Molar ratios of reactants may be used. Alternatively, molar excesses of phenol can be employed, i.e., 2 to 3 equivalents of phenol for each equivalent of olefin with unreacted phenol recycled. The latter process maximizes monoalkylphenol. Examples of inert solvents include heptane, benzene, toluene, chlorobenzene and 250 thinner which is a mixture of aromatics, paraffins and naphthenes.

The polyalkyl substituent on the polyalkylphenols employed in the invention is generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The preferred polyisobutenes used to prepare the presently employed polyalkylphenols are polyisobutenes which comprise at least about 20% of the more reactive methylvinylidene isomer, preferably at least 50% and more preferably at least 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808. Such polyisobutenes, known as "reactive" polyisobutenes, yield high molecular weight alcohols in which the hydroxyl group is at or near the end of the hydrocarbon chain. Examples of suitable polyisobutenes having a high alkylvinylidene content include Ultravis 30, a polyisobutene having a number average molecular weight of about 1300 and a methylvinylidene content of about 74%, and Ultravis 10, a polyisobutene having a number average molecular weight of about 950 and a methylvinylidene content of about 76%, both available from British Petroleum.

The alkylene carbonates of formula III are known compounds which are available commercially or can be readily prepared using conventional procedures. Suitable alkylene carbonates include ethylene carbonate, propylene carbonate, 1,2-butylene carbonate, 2,3-butylene carbonate, and the like. A preferred alkylene carbonate is ethylene carbonate.

The catalyst employed in the reaction of the polyalkylphenol and alkylene carbonate may be any of the well known hydroxyalkylation catalysts. Typical hydroxyalkylation catalysts include alkali metal hydrides, such as lithium hydride, sodium hydride and potassium hydride, alkali metal hydroxides, such as sodium hydroxide and potassium hydroxide, and alkali metal salts, for example, alkali metal halides, such as sodium chloride and potassium chloride, and alkali metal carbonates, such as sodium carbonate and potassium carbonate. The amount of catalyst employed will generally range from about 0.01 to 1.0 equivalent, preferably from about 0.05 to 0.3 equivalent.

The polyalkylphenol and alkylene carbonate are generally reacted in essentially equivalent amounts in the presence of the hydroxyalkylation catalyst at a temperature in the range of about 100° C. to 210° C., and preferably from about 150° C. to about 170° C. The reaction may take place in the presence or absence of an inert solvent.

The time of reaction will vary depending on the particular alkylphenol and alkylene carbonate reactants, the catalyst used and the reaction temperature. Generally, the reaction time will range from about two hours to about five hours. The progress of the reaction is typically monitored by the evolution of carbon dioxide. At the completion of the reaction, the polyalkylphenoxyalkanol product is isolated using conventional techniques.

The hydroxyalkylation reaction of phenols with alkylene carbonates is well known in the art and is described, for example, in U.S. Pat. Nos. 2,987,555; 2,967,892; 3,283,030 and 4,341,905.

Alternatively, the polyalkylphenoxyalkanol product of formula IV may be prepared by reacting the polyalkylphenol of formula II with an alkylene oxide of the formula:

(V)

wherein $R_2$ and $R_3$ are as defined herein, in the presence of a hydroxyalkylation catalyst as described above. Suitable alkylene oxides of formula V include ethylene oxide, propylene oxide, 1,2-butylene oxide, 2,3-butylene oxide, and the like. A preferred alkylene oxide is ethylene oxide.

In a manner similar to the reaction with alkylene carbonate, the polyalkylphenol and alkylene oxide are reacted in essentially equivalent or equimolar amounts in the presence of 0.01 to 1.0 equivalent of a hydroxyalkylation catalyst, such as sodium or potassium hydride, at a temperature in the range of about 30° C. to about 150° C., for about 2 to about 24 hours. The reaction may be conducted in the presence or absence of a substantially anhydrous inert solvent. Suitable solvents include toluene, xylene, and the like. Generally, the reaction conducted at a pressure sufficient to contain the reactants and any solvent present, typically at atmospheric or higher pressure. Upon completion of the reaction, the polyalkylphenoxyalkanol is isolated by conventional procedures.

The polyalkylphenoxyalkanol of formula IV is subsequently reacted with a substituted benzoic acid of formula VI to provide the aromatic ester compounds of formula I. This reaction can be represented as follows:

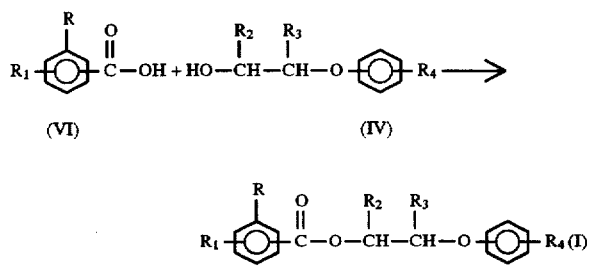

wherein R, $R_1$, $R_2$, $R_3$ and $R_4$ are as defined herein, and wherein any hydroxy or amino substituent on the substituted benzoic acid of formula VI is preferably protected with a suitable protecting group, for example, a benzyl or nitro group, respectively. Moreover, a —$CH_2NH_2$ substituent on the aromatic ring will preferably be protected by the use of a cyano group, CN.

This reaction is typically conducted by contacting a polyalkylphenoxyalkanol of formula IV with about 0.25 to about 1.5 molar equivalents of the corresponding substituted and protected benzoic acid of formula VI in the presence of an acidic catalyst at a temperature in the range of about 70° C. to about 160° C. for about 0.5 to about 48 hours. Suitable acid catalysts for this reaction include p-toluene sulfonic acid, methanesulfonic acid and the like. Optionally, the reaction can be conducted in the presence of an inert solvent, such as benzene, toluene and the like. The water generated by this reaction is preferably removed during the course of the reaction, for example, by azeotropic distillation.

The substituted benzoic acids of formula VI are generally known compounds and can be prepared from known compounds using conventional procedures or obvious modifications thereof. Representative acids suitable for use as starting materials include, for example, 2-aminobenzoic acid (anthranilic acid), 3-aminobenzoic acid, 4-aminobenzoic acid, 3-amino-4-hydroxybenzoic acid, 4-amino-3-hydroxybenzoic acid, 2-nitrobenzoic acid, 3-nitrobenzoic acid, 4-nitrobenzoic acid, 3-hydroxy-4-nitrobenzoic acid, 4-hydroxy-3-nitrobenzoic acid. When the R substituent is —$CH_2$—$NR_5R_6$, suitable starting materials include 4-cyanobenzoic acid and 3-cyanobenzoic acid.

Preferred substituted benzoic acids include 3-nitrobenzoic acid, 4-nitrobenzoic acid, 3-hydroxy-4-nitrobenzoic acid, 4-hydroxy-3-nitrobenzoic acid, 3-cyanobenzoic acid and 4-cyanobenzoic acid.

The compounds of formula I or their suitably protected analogs also can be prepared by reacting the polyalkylphenoxyalkanol of formula IV with an acid halide of the substituted benzoic acid of formula VI such as an acid chloride or acid bromide. This can be represented by the following reaction equation:

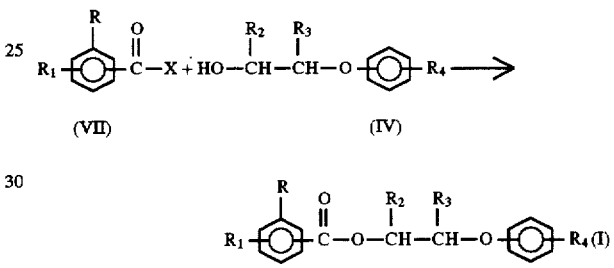

wherein X is halide, typically chloride or bromide, and R, $R_1$, $R_2$, $R_3$ and $R_4$ are as defined herein above, and wherein any hydroxy or amino substituents on the acid halide of formula VII are preferably protected with a suitable protection group, for example, benzyl or nitro, respectively. Also, when R is —$CH_2NR_5R_6$, a suitable starting material is a cyanobenzoyl halide.

Typically, this reaction is conducted by contacting the polyalkylphenoxyalkanol of formula IV with about 0.9 to about 1.5 molar equivalents of the acid halide of formula VII in an inert solvent, such as, for example, toluene, dichloromethane, diethyl ether, and the like, at a temperature in the range of about 25° C. to about 150° C. The reaction is generally complete in about 0.5 to about 48 hours. Preferably, the reaction is conducted in the presence of a sufficient amount of an amine capable of neutralizing the acid generated during the reaction, such as, for example, triethylamine, di(isopropyl)ethylamine, pyridine or 4-dimethylaminopyridine.

When the benzoic acids of formula VI or acid halides of formula VII contain a hydroxyl group, protection of the aromatic hydroxyl groups may be accomplished using well-known procedures. The choice of a suitable protecting group for a particular hydroxybenzoic carboxylic acid will be apparent to those skilled in the art. Various protecting groups, and their introduction and removal, are described, for example, in T. W. Greene and P. G. M. Wuts, *Protective Groups in organic Synthesis*, Second Edition, Wiley, New York, 1991, and references cited therein.

After completion of the esterification, deprotection of the aromatic hydroxyl group can also be accomplished using conventional procedures. Appropriate conditions for this deprotection step will depend upon the protecting group(s)

utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction is conducted in an inert solvent, preferably a mixture of ethyl acetate and acetic acid, at a temperature of from about 0C. to about 40° C. for about 1 to about 24 hours.

When the benzoic acids of formula VI or acyl halides of formula VII have a free amino group (—$NH_2$) on the phenyl moiety, it is generally desirable to first prepare the corresponding nitro compound (i.e., where R and/or $R_1$ is a nitro group) using the above-described synthetic procedures, including preparation of the acyl halides, and then reduce the nitro group to an amino group using conventional procedures. Aromatic nitro groups may be reduced to amino groups using a number of procedures that are well known in the art. For example, aromatic nitro groups may be reduced under catalytic hydrogenation conditions; or by using a reducing metal, such as zinc, tin, iron and the like, in the presence of an acid, such as dilute hydrochloric acid. Generally, reduction of the nitro group by catalytic hydrogenation is preferred. Typically, this reaction is conducted using about 1 to 4 atmospheres of hydrogen and a platinum or palladium catalyst, such as palladium on carbon. The reaction is typically carried out at a temperature of about 0° C. to about 100° C. for about 1 to 24 hours in an inert solvent, such as ethanol, ethyl acetate and the like. Hydrogenation of aromatic nitro groups is discussed in further detail in, for example, P. N. Rylander, *Catalytic Hydrogenation in organic Synthesis*, pp. 113–137, Academic Press (1979); and *Organic Synthesis, Collective Vol. 1*, Second Edition, pp. 240–241, John Wiley & Sons, Inc. (1941); and references cited therein.

Likewise, when the benzoic acids of formula VI or acyl halides of formula VII contain a —$CH_2NH_2$ group on the phenyl moiety, it is generally desirable to first prepare the corresponding cyano compounds (i.e., where R and/or $R_1$ is a —CN group), and then reduce the cyano group to a —$CH_2NH_2$ group using conventional procedures. Aromatic cyano groups may be reduced to —$CH_2NH_2$ groups using procedures well known in the art. For example, aromatic cyano groups may be reduced under catalytic hydrogenation conditions similar to those described above for reduction of aromatic nitro groups to amino groups. Thus, this reaction is typically conducted using about 1 to 4 atmospheres of hydrogen and a platinum or palladium catalyst, such as palladium on carbon. Another suitable catalyst is a Lindlar catalyst, which is palladium on calcium carbonate. The hydrogenation may be carried out at temperatures of about 0° C. to about 100° C. for about 1 to 24 hours in an inert solvent such as ethanol, ethyl acetate, and the like. Hydrogenation of aromatic cyano groups is further discussed in the references cited above for reduction of aromatic nitro groups.

The acyl halides of formula VII can be prepared by contacting the corresponding benzoic acid compound of formula VI with an inorganic acid halide, such as thionyl chloride, phosphorous trichloride, phosphorous tribromide, or phosphorous pentachloride; or with oxalyl chloride. Typically, this reaction will be conducted using about 1 to 5 molar equivalents of the inorganic acid halide or oxalyl chloride, either neat or in an inert solvent, such as diethyl ether, at a temperature in the range of about 20° C. to about 80° C. for about 1 to about 48 hours. A catalyst, such as N,N-dimethylformamide, may also be used in this reaction. Again it is preferred to first protect any hydroxy or amino substituents before converting the benzoic acid to the acyl halide.

The Poly(oxyalkylene) Amine

The poly(oxyalkylene) amine component of the present fuel additive composition is a poly(oxyalkylene) amine having at least one basic nitrogen atom and a sufficient number of oxyalkylene units to render the poly(oxyalkylene) amine soluble in hydrocarbons boiling in the gasoline or diesel range.

Preferably, such poly(oxyalkylene) amines will also be of sufficient molecular weight so as to be nonvolatile at normal engine intake valve operating temperatures, which are generally in the range of about 200° C to 250° C.

Generally, the poly(oxyalkylene) amines suitable for use in the present invention will contain at least about 5 oxyalkylene units, preferably about 5 to 100, more preferably about 8 to 100, and even more preferably about 10 to 100. Especially preferred poly(oxyalkylene) amines will contain about 10 to 25 oxyalkylene units.

The molecular weight of the presently employed poly (oxyalkylene) amines will generally range from about 500 to about 10,000, preferably from about 500 to about 5,000.

Suitable poly(oxyalkylene) amine compounds for use in the present invention include hydrocarbyl poly(oxyalkylene) polyamines as disclosed, for example, in U.S. Pat. No. 4,247,301, issued Jan. 27, 1981 to Honnen, the disclosure of which is incorporated herein by reference. These compounds are hydrocarbyl poly(oxyalkylene) polyamines wherein the poly(oxyalkylene) moiety comprises at least one hydrocarbyl-terminated poly(oxyalkylene) chain of 2 to 5 carbon atom oxyalkylene units, and wherein the poly (oxyalkylene) chain is bonded through a terminal carbon atom to a nitrogen atom of a polyamine having from 2 to about 12 amine nitrogen atoms and from 2 to about 40 carbon atoms with a carbon-to-nitrogen ratio between about 1:1 and 10:1. The hydrocarbyl group on these hydrocarbyl poly(oxyalkylene) polyamines will contain from about 1 to 30 carbon atoms. These compounds generally have molecular weights in the range of about 500 to 10,000, preferably from about 500 to 5,000 and more preferably from about 800 to 5,000.

The above-described hydrocarbyl poly(oxyalkylene) polyamines are prepared by conventional procedures known in the art, as taught, for example, in U.S. Pat. No. 4,247,301.

Other poly(oxyalkylene) amines suitable for use in the present invention are the poly(oxyalkylene) polyamines wherein the poly(oxyalkylene) moiety is connected to the polyamine moiety through an oxyalkylene hydroxy-type linkage derived from an epihalohydrin, such as epichlorohydrin or epibromohydrin. This type of poly(oxyalkylene) amine having an epihalohydrin-derived linkage is described, for example, in U.S. Pat. No. 4,261,704, issued Apr. 14, 1981 to Langdon, the disclosure of which is incorporated herein by reference.

Useful polyamines for preparing the epihalohydrin-derived poly(oxyalkylene) polyamines include, for example, alkylene polyamines, polyalkylene polyamines, cyclic amines, such as piperazines, and amino-substituted amines. The poly(oxyalkylene) polyamines having an epihalohydrin-derived linkage between the poly (oxyalkylene) and polyamine moieties are prepared using known procedures as taught, for example, in U.S. Pat. No. 4,261,704.

Another type of poly(oxyalkylene) amine useful in the present invention is a highly branched alkyl poly (oxyalkylene) monoamine as described, for example in U.S. Pat. No. 5,094,667, issued Mar. 10, 1992 to Schilowitz et al., the disclosure of which is incorporated herein by reference. These highly branched alkyl poly(oxyalkylene) monoamines have the general formula:

$$R_7-O-(C_4H_8O)_p CH_2CH_2CH_2NH_2 \quad (VIII)$$

wherein $R_7$ is a highly branched alkyl group containing from 12 to 40 carbon atoms, preferably an alkyl group having 20 carbon atoms which is derived from a Guerbet condensation reaction, and p is a number up to 30, preferably 4 to 8. The preferred alkyl group is derived from a Guerbet alcohol containing 20 carbon atoms having the formula:

$$\begin{array}{c} R_8-CHCH_2OH \\ | \\ CH_2CH_2R_8 \end{array} \quad (IX)$$

wherein $R_8$ is a hydrocarbyl chain.

The above highly branched alkyl poly(oxyalkylene) monoamines are prepared by using known methods as disclosed, for example, in U.S. Pat. No. 5,094,667.

A preferred class of poly(oxyalkylene) amine for use in the fuel additive composition of the present invention are hydrocarbyl poly(oxyalkylene) monoamines as described, for example, in U.S. Pat. No. 5,112,364, issued May 12, 1992 to Rath et al., the disclosure of which is incorporated herein by reference. As disclosed in U.S. Pat. No. 5,112,364, such poly(oxyalkylene) monoamines may be prepared by the reductive amination of a phenol-initiated or alkylphenol-initiated poly(oxyalkylene) alcohol with ammonia or a primary amine.

In addition, the above-mentioned U.S. Pat. No. 4,247,301 to Honnen discloses hydrocarbyl poly(oxyalkylene) monoamines which are suitable for use in the present fuel additive composition. In particular, Example 6 of this patent describes alkylphenyl poly(oxyalkylene) monoamines prepared from ammonia and dimethylamine.

A particularly preferred type of hydrocarbyl poly(oxyalkylene) monoamine is an alkylphenyl poly(oxyalkylene) monoamine wherein the poly(oxyalkylene) moiety contains oxypropylene units or oxybutylene units or mixtures of oxypropylene and oxybutylene units. Preferably, the alkyl group on the alkylphenyl moiety is a straight or branched-chain alkyl of 1 to 24 carbon atoms. An especially preferred alkylphenyl moiety is tetrapropenylphenyl, that is, where the alkyl group is a branched-chain alkyl of 12 carbon atoms derived from propylene tetramer.

A further discussion of the hydrocarbon-substituted poly(oxyalkylene) moiety on the poly(oxyalkylene) amine component of the present fuel additive composition is found hereinbelow.

Another preferred class of poly(oxyalkylene) amine for use in the fuel additive composition of the present invention are hydrocarbyl-substituted poly(oxyalkylene) aminocarbamates disclosed, for example, in U.S. Pat. Nos. 4,288,612; 4,236,020; 4,160,648; 4,191,537; 4,270,930; 4,233,168; 4,197,409; 4,243,798 and 4,881,945, the disclosure of each of which are incorporated herein by reference.

These hydrocarbyl poly(oxyalkylene) aminocarbamates contain at least one basic nitrogen atom and have an average molecular weight of about 500 to 10,000, preferably about 500 to 5,000, and more preferably about 1,000 to 3,000. As described more fully hereinbelow, these hydrocarbyl poly(oxyalkylene) aminocarbamates contain (a) a poly(oxyalkylene) moiety, (b) an amine moiety and (c) a carbamate connecting group.

A. The Poly(oxyalkylene) Moiety

The hydrocarbyl-terminated poly(oxyalkylene) polymers which are utilized in preparing the hydrocarbyl poly(oxyalkylene) aminocarbamates employed in the present invention are monohydroxy compounds, e.g., alcohols, often termed monohydroxy polyethers, or polyalkylene glycol monocarbyl ethers, or "capped" poly(oxyalkylene) glycols, and are to be distinguished from the poly(oxyalkylene) glycols (diols), or polyols, which are not hydrocarbyl-terminated, i.e., are not capped. These hydrocarbyl poly(oxyalkylene) alcohols may be produced by the addition of lower alkylene oxides, such as ethylene oxide, propylene oxide, butylene oxide, etc. to a hydroxy compound, $R_9OH$, under polymerization conditions, wherein $R_9$ is the hydrocarbyl group which caps the poly(oxyalkylene) chain.

In the hydrocarbyl poly(oxyalkylene) aminocarbamates employed in the present invention, the hydrocarbyl group $R_9$ will generally contain from 1 to about 30 carbon atoms, preferably from 2 to about 20 carbon atoms and is preferably aliphatic or aromatic, i.e., an alkyl or alkyl phenyl wherein the alkyl is a straight or branched-chain of from 1 to about 24 carbon atoms. More preferably, $R_9$ is alkylphenyl wherein the alkyl group is a branched-chain of 12 carbon atoms, derived from propylene tetramer, and commonly referred to as tetrapropenyl.

The oxyalkylene units in the poly(oxyalkylene) moiety preferably contain from 2 to about 5 carbon atoms but one or more units of a larger carbon number may also be present. Generally, each poly(oxyalkylene) polymer contains at least about 5 oxyalkylene units, preferably about 5 to about 100 oxyalkylene units, more preferably about 8 to about 100 units, even more preferably about 10 to 100 units, and most preferably 10 to about 25 such units. The poly(oxyalkylene) moiety of the hydrocarbyl poly(oxyalkylene) aminocarbamates employed in the present invention is more fully described and exemplified in U.S. Pat. No. 4,191,537, issued Mar. 4, 1980 to Lewis, the disclosure of which is incorporated herein by reference.

Although the hydrocarbyl group on the hydrocarbyl poly(oxyalkylene) moiety will preferably contain from 1 to about 30 carbon atoms, longer hydrocarbyl groups, particularly longer chain alkyl phenyl groups, may also be employed. For example, alkylphenyl poly(oxyalkylene) aminocarbamates wherein the alkyl group contains at least 40 carbon atoms, as described in U.S. Pat. No. 4,881,945, issued Nov. 21, 1989 to Buckley, are also contemplated for use in the present invention. The alkyl phenyl group on the aminocarbamates of U.S. Pat. No. 4,881,945 will preferably contain an alkyl group of 50 to 200 carbon atoms, and more preferably, an alkyl group of 60 to 100 carbon atoms. These longer chain alkyl groups will generally be derived from olefin polymers, such as polybutene. The disclosure of U.S. Pat. No. 4,881,945 is incorporated herein by reference.

Also contemplated for use in the present invention are alkylphenyl poly(oxypropylene) aminocarbamates wherein the alkyl group is a substantially straight-chain alkyl group of about 25 to 50 carbon atoms derived from an alpha olefin oligomer of $C_8$ to $C_{20}$ alpha olefins, as described in PCT International Pat. Application Publication No. WO 90/07564, published July 12, 1990, the disclosure of which is incorporated herein by reference.

B. The Amine Moiety

The amine moiety of the hydrocarbyl poly(oxyalkylene) aminocarbamate is preferably derived from a polyamine having from 2 to about 12 amine nitrogen atoms and from 2 to about 40 carbon atoms.

The polyamine is preferably reacted with a hydrocarbyl poly(oxyalkylene) chloroformate to produce the hydrocarbyl poly(oxyalkylene) aminocarbamate fuel additive finding use within the scope of the present invention. The chloroformate is itself derived from the hydrocarbyl poly(oxyalkylene) alcohol by reaction with phosgene.

The polyamine provides the hydrocarbyl poly(oxyalkylene) aminocarbamate with, on the average, at least about one basic nitrogen atom per carbamate molecule, i.e., a nitrogen atom titratable by strong acid. The polyamine preferably has a carbon-to-nitrogen ratio of from about 1:1 to about 10:1. The polyamine may be substituted with substituents selected from hydrogen, hydrocarbyl groups of from 1 to about 10 carbon atoms, acyl groups of from 2 to about 10 carbon atoms, and monoketone, monohydroxy, mononitro, monocyano, alkyl and alkoxy derivatives of hydrocarbyl groups of from 1 to 10 carbon atoms. It is preferred that at least one of the basic nitrogen atoms of the polyamine is a primary or secondary amino nitrogen. The amine moiety of the hydrocarbyl poly(oxyalkylene) aminocarbamates employed in the present invention has been described and exemplified more fully in U.S. Pat. No. 4,191,537.

A more preferred polyamine for use in preparing the hydrocarbyl poly(oxyalkylene) aminocarbamates finding use within the scope of the present invention is a polyalkylene polyamine, including alkylenediamine, and including substituted polyamines, e.g., alkyl and hydroxyalkyl-substituted polyalkylene polyamine. Preferably, the alkylene group contains from 2 to 6 carbon atoms, there being preferably from 2 to 3 carbon atoms between the nitrogen atoms. Examples of such polyamines include ethylenediamine, diethylenetriamine, triethylenetetramine, di(trimethylene)triamine, dipropylenetriamine, tetraethylenepentamine, etc.

Among the polyalkylene polyamines, polyethylene polyamine and polypropylene polyamine containing 2 to about 12 amine nitrogen atoms and 2 to about 24 carbon atoms are especially preferred and in particular, the lower polyalkylene polyamines, e.g., ethylenediamine, diethylenetriamine, propylenediamine, dipropylenetriamine, etc., are most preferred.

C. The Aminocarbamate Connecting Group

The hydrocarbyl poly(oxyalkylene) aminocarbamate employed as the poly(oxyalkylene) amine component of the fuel additive composition of the present invention is obtained by linking the polyamine and the hydrocarbyl poly(oxyalkylene) alcohol together through a carbamate linkage, i.e.,

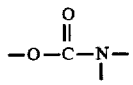

wherein the oxygen may be regarded as the terminal hydroxyl oxygen of the poly(oxyalkylene) alcohol, the nitrogen is derived from the polyamine and the carbonyl group —C(O)—, is preferably provided by a coupling agent, such as phosgene.

In a preferred method of preparation, the hydrocarbyl poly(oxyalkylene) alcohol is reacted with phosgene to produce a chloroformate and the chloroformate is reacted with the polyamine. Since there may be more than one nitrogen atom of the polyamine which is capable of reacting with the chloroformate, the carbamate product may contain more than one hydrocarbyl poly(oxyalkylene) moiety. It is preferred that the hydrocarbyl poly(oxyalkylene) aminocarbamate product contains on the average, about one poly(oxyalkylene) moiety per molecule (i.e., is a monocarbamate), although it is understood that this reaction route may lead to mixtures containing appreciable amounts of di- or higher poly(oxyalkylene) chain substitution on a polyamine containing several reactive nitrogen atoms.

A particularly preferred aminocarbamate is alkylphenyl poly(oxybutylene) aminocarbamate, wherein the amine moiety is derived from ethylene diamine or diethylene triamine. Synthetic methods to avoid higher degrees of substitution, methods of preparation, and other characteristics of the aminocarbamates used in the present invention are more fully described and exemplified in U.S. Pat. No. 4,191,537.

Fuel Compositions

The fuel additive composition of the present invention will generally be employed in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

Generally, the present fuel additive composition will be employed in a hydrocarbon fuel in a concentration ranging from about 50 to about 5,000 parts per million (ppm) by weight, preferably from 100 to 2,500 ppm.

In terms of individual components, hydrocarbon fuel containing the fuel additive composition of this invention will generally contain about 25 to 2,000 ppm of the polyalkylphenoxyalkyl aromatic ester component and about 25 to 2,000 ppm of the poly(oxyalkylene) amine component. The ratio of the polyalkylphenoxyalkyl aromatic ester to poly(oxyalkylene) amine will generally range from about 0.05:1 to about 5:1, and will preferably be about 2:1 or less.

The fuel additive composition of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additive composition of the present invention, including, for example, oxygenates, such as t-butyl methyl ether, antiknock agents, such as methylcyclopentadienyl manganese tricarbonyl, and other dispersants/detergents, such as hydrocarbyl amines, or succinimides. Additionally, antioxidants, metal deactivators, demulsifiers and carburetor or fuel injector detergents may be present.

In diesel fuels, other well-known additives can be employed, such as pour point depressants, flow improvers, cetane improvers, and the like.

A fuel-soluble, nonvolatile carrier fluid or oil may also be used with the fuel additive composition of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic fluid, such as mineral oil, refined petroleum oils, synthetic polyalkanes and alkenes, including hydrogenated and unhydrogenated polyalphaolefins, and synthetic polyoxyalkylene-derived fluids, such as those described, for example, in U.S. Pat. No. 4,191,537 to Lewis, and polyesters, such as those described, for example, in U.S. Pat. Nos. 3,756,793 to Robinson and 5,004,478 to Vogel et al., and in European patent application Nos. 356,726, published Mar. 7, 1990, and 382,159, published Aug. 16, 1990.

These carrier fluids are believed to act as a carrier for the fuel additive composition of the present invention and to assist in removing and retarding deposits. The carrier fluid may also exhibit synergistic deposit control properties when used in combination with the fuel additive composition of this invention.

The carrier fluids are typically employed in amounts ranging from about 25 to about 5000 ppm by weight of the hydrocarbon fuel, preferably from 100 to 3000 ppm of the fuel.

Preferably, the ratio of carrier fluid to deposit control additive will range from about 0.2:1 to about 10:1, more preferably from 0.5:1 to 3:1.

When employed in a fuel concentrate, carrier fluids will generally be present in amounts ranging from about 20 to about 60 weight percent, preferably from 30 to 50 weight percent.

PREPARATIONS AND EXAMPLES

A further understanding of the invention can be had in the following nonlimiting Examples. Wherein unless expressly stated to the contrary, all temperatures and temperature ranges refer to the Centigrade system and the term "ambient" or "room temperature" refers to about 20° C. to 25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 300 mHz, signals are assigned as singlets (s), broad singlets (bs), doublets (d), double doublets (dd), triplets (t), double triplets (dt), quartets (q), and multiplets (m), and cps refers to cycles per second.

EXAMPLE 1

Preparation of Polyisobutyl Phenol

To a flask equipped with a magnetic stirrer, reflux condenser, thermometer, addition funnel and nitrogen inlet was added 203.2 grams of phenol. The phenol was warmed to 40° C. and the heat source was removed. Then, 73.5 milliliters of boron trifluoride etherate was added dropwise. 1040 grams of Ultravis 10 Polyisobutene (molecular weight 950, 76% methylvinylidene, available from British Petroleum) was dissolved in 1,863 milliliters of hexane. The polyisobutene was added to the reaction at a rate to maintain the temperature between 22° C. to 27° C. The reaction mixture was stirred for 16 hours at room temperature. Then, 400 milliliters of concentrated ammonium hydroxide was added, followed by 2,000 milliliters of hexane. The reaction mixture was washed with water (3×2,000 milliliters), dried over magnesium sulfate, filtered and the solvents removed under vacuum to yield 1,056.5 grams of a crude reaction product. The crude reaction product was determined to contain 80% of the desired product by proton NMR and chromatography on silica gel eluting with hexane, followed by hexane: ethylacetate: ethanol (93:5:2).

EXAMPLE 2

Preparation of

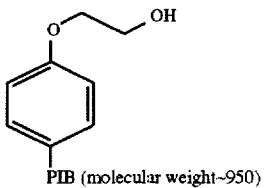

PIB (molecular weight~950)

1.1 grams of a 35 weight percent dispersion of potassium hydride in mineral oil and 4-polyisobutyl phenol (99.7 grams, prepared as in Example 1) were added to a flask equipped with a magnetic stirrer, reflux condensor, nitrogen inlet and thermometer. The reaction was heated at 130° C. for one hour and then cooled to 100° C. Ethylene carbonate (8.6 grams) was added and the mixture was heated at 160 C for 16 hours. The reaction was cooled to room temperature and one milliliter of isopropanol was added. The reaction was diluted with one liter of hexane, washed three times with water and once with brine. The organic layer was dried over anhydrous magnesium sulfate, filtered and the solvents removed in vacuo to yield 98.0 grams of the desired product as a yellow oil.

EXAMPLE 3

Preparation of

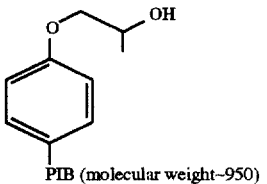

PIB (molecular weight~950)

15 grams of a 35 weight percent dispersion of potassium hydride in mineral oil and 4-polyisobutyl phenol (1378.5 grams, prepared as in Example 1) were added to a flask equipped with a mechanical stirrer, reflux condenser, nitrogen inlet and thermometer. The reaction was heated at 130° C. for one hour and then cooled to 100° C. Propylene carbonate (115.7 milliliters) was added and the mixture was heated at 160° C. for 16 hours. The reaction was cooled to room temperature and ten milliliters of isopropanol were added. The reaction was diluted with ten liters of hexane, washed three times with water and once with brine. The organic layer was dried over anhydrous magnesium sulfate, filtered and the solvents removed in vacuo to yield 1301.7 grams of the desired product as a yellow oil.

EXAMPLE 4

Preparation of

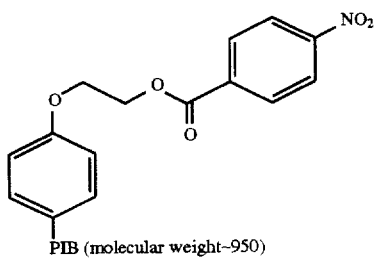
PIB (molecular weight–950)

To a flask equipped with a magnetic stirrer, thermometer, Dean-Stark trap, reflux condensor and nitrogen inlet was added 15.0 grams of the alcohol from Example 2, 2.6 grams of 4-nitrobenzoic acid and 0.24 grams of p-toluenesulfonic acid. The mixture was stirred at 130° C. for sixteen hours, cooled to room temperature and diluted with 200 mL of hexane. The organic phase was washed twice with saturated aqueous sodium bicarbonate followed by once with saturated aqueous sodium chloride. The organic layer was then dried over anhydrous magnesium sulfate, filtered and the solvents removed in vacuo to yield 15.0 grams of the desired product as a brown oil. The oil was chromatographed on silica gel, eluting with hexane/ethyl acetate (9:1) to afford 14.0 grams of the desired ester as a yellow oil. $^1$H NMR (CDCl$_3$) d 8.3 (AB quartet, 4H), 7.25 (d, 2H), 6.85 (d, 2H), 4.7 (t, 2H), 4.3 (t, 2H), 0.7–1.6 (m, 137H).

EXAMPLE 5

Preparation of

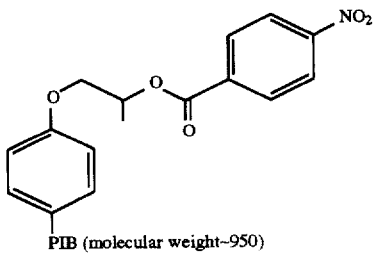
PIB (molecular weight–950)

To a flask equipped with a magnetic stirrer, thermometer, Dean-Stark trap, reflux condenser and nitrogen inlet was added 15.0 grams of the alcohol from Example 3, 2.7 grams of 4-nitrobenzoic acid and 0.23 grams of p-toluenesulfonic acid. The mixture was stirred at 130° C. for sixteen hours, cooled to room temperature and diluted with 200 mL of hexane. The organic phase was washed twice with saturated aqueous sodium bicarbonate followed by once with saturated aqueous sodium chloride. The organic layer was then dried over anhydrous magnesium sulfate, filtered and the solvents removed in vacuo to yield 16.0 grams of the desired product as a brown oil. The oil was chromatographed on silica gel, eluting with hexane/ethyl acetate (8:2) to afford 15.2 grams of the desired ester as a brown oil. 1H NMR (CDCl$_3$) d 8.2 (AB quartet, 4H), 7.25 (d, 2H), 6.85 (d, 2H), 5.55 (hx, 1H), 4.1 (t, 2H), 0.6–1.8 (m, 140H).

EXAMPLE 6

Preparation of

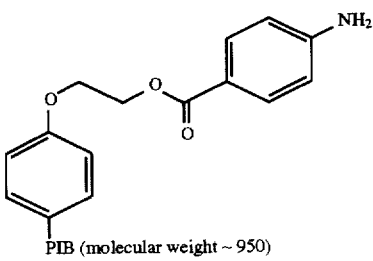
PIB (molecular weight ~ 950)

A solution of 9.4 grams of the product from Example 4 in 100 milliliters of ethyl acetate containing 1.0 gram of 10% palladium on charcoal was hydrogenolyzed at 35–40 psi for 16 hours on a Parr low-pressure hydrogenator. Catalyst filtration and removal of the solvent in vacuo yield 7.7 grams of the desired product as a yellow oil. $^1$H NMR (CDCl$_3$) d 7.85 (d, 2H), 7.3 (d, 2H), 6.85 (d, 2H), 6.6 (d, 2H), 4.6 (t, 2H), 4.25 (t, 2H), 4.05 (bs, 2H), 0.7–1.6 (m, 137H).

EXAMPLE 7

Preparation of

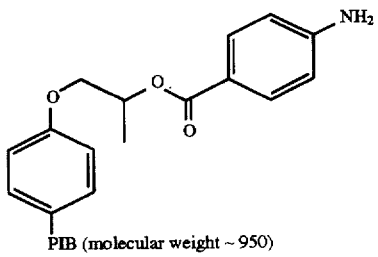
PIB (molecular weight ~ 950)

A solution of 15.2 grams of the product from Example 5 in 200 milliliters of ethyl acetate containing 1.0 gram of 10% palladium on charcoal was hydrogenolyzed at 35–40 psi for 16 hours on a Parr low-pressure hydrogenator. Catalyst filtration and removal of the solvent in vacuo yield 15.0 grams of the desired product as a brown oil. $^1$H NMR (CDCl$_3$/D$_2$O) d 7.85 (d, 2H), 7.25 (d, 2H), 6.85 (d, 2H), 6.6 (d, 2H), 5.4 (hx, 1H), 3.8–4.2 (m, 4H), 0.6–1.8 (m, 140H).

EXAMPLE 8

Preparation of Dodecylphenoxy Poly(oxybutylene) poly(oxypropylene) Amine

A dodecylphenoxypoly(oxybutylene)poly(oxypropylene) amine was prepared by the reductive amination with ammonia of the random copolymer poly(oxyalkylene) alcohol, dodecylphenoxy poly(oxybutylene)poly(oxypropylene) alcohol, wherein the alcohol has an average molecular weight of about 1598. The poly(oxyalkylene) alcohol was prepared from dodecylphenol using a 75/25 weight/weight ratio of butylene oxide and propylene oxide, in accordance with the procedures described in U.S. Pat. Nos. 4,191,537; 2,782,240 and 2,841,479, as well as in Kirk-Othmer, "Encyclopedia of Chemical Technology", 4th edition, Volume 19, 1996, page 722. The reductive amination of the poly (oxyalkylene) alcohol was carried out using conventional techniques as described in U.S. Pat. Nos. 5,112,364; 4,609, 377 and 3,440,029.

EXAMPLE 9

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the valve at the end of the run. The differences between the two weights is the weight of the deposit. A lesser amount of deposit indicates a superior additive. The operating conditions of the test were as follows: water jacket temperature 200° F.; intake manifold vacuum of 12 in. Hg, air-fuel ratio of 12, ignition spark timing of 40 BTC; engine speed is 1800 rpm; the crankcase oil is a commercial 30W oil.

The amount of carbonaceous deposit in milligrams on the intake valves is reported for each of the test compounds in Table I.

TABLE I

| | Intake Valve Deposit Weight (in milligrams) | | |
|---|---|---|---|
| Sample[1] | Run 1 | Run 2 | Average |
| Base Fuel | 354.9 | 333.5 | 344.2 |
| Example 4 | 169.0 | 178.0 | 173.5 |
| Example 6 | 13.4 | 12.2 | 12.8 |

[1]At 150 parts per million actives (ppma).

The base fuel employed in the above single-cylinder engine tests was a regular octane unleaded gasoline containing no fuel detergent. The test compounds were admixed with the base fuel to give a concentration of 150 ppma (parts per million actives).

The data in Table I illustrates the significant reduction in intake valve deposits provided by the aromatic ester component of the present invention (Examples 4 and 6) compared to the base fuel.

EXAMPLE 10

Multicylinder Engine Test

The fuel additive composition of the present invention was tested in a laboratory multicylinder engine to evaluate their intake valve and combustion chamber deposit control performance. The test engine was a 2.3 liter, port fuel injected, 4-cylinder single overhead cam engine manufactured by Ford Motor Company. The major engine dimensions are set forth in Table II.

TABLE II

| Engine Dimensions | |
|---|---|
| Bore | 9.60 cm |
| Stroke | 7.94 cm |
| Displacement Volume | 2.30 liter |
| Compression Ratio | 9.50:1 |

The test engine was operated for 60 hours (24 hours a day) on a test cycle developed by the Coordinating Research Council (CRC). The cycle for engine operation during the test is set forth in Table III.

TABLE III

| Engine Operating Cycle | | | |
|---|---|---|---|
| Stage | Length of Time[1] (Min:Sec) | Engine Speed [RPM] | Manifold Absolute Pressure [mm Hg] |
| 1 | 4:00 | 2000 ± 10 | 230 ± 10 |
| 2 | 8:00 | 2800 ± 10 | 540 ± 10 |

[1]All stages include a 30 second transition ramp.

All of the test runs were made with the same base gasoline, which was representative of commercial unleaded fuel. The results are set forth in Table IV.

TABLE IV

| Multicylinder Engine Test Results | | | |
|---|---|---|---|
| Sample | Conc. (ppma) | Intake Valve Deposits, mg | Combustion Chamber Deposits, mg |
| Base Fuel | — | 521 | 945 |
| Aromatic Ester/ Carrier Fluid[1] | 50/50 | 657 | 1262 |
| Aromatic Ester/ Poly (oxyalkylene) Amine[2] | 50/50 | 262 | 1087 |

[1]Mixture of 50 ppm of 4-polyisobutylphenoxyethyl para-aminobenzoate prepared as described in Example 6 and 50 ppm of a dodecylphenoxypoly (oxybutylene) alcohol carrier fluid.
[2]Mixture of 50 ppm of 4-polyisobutylphenoxyethyl para-aminobenzoate and 50 ppm of dodecylphenoxy poly(oxybutylene)poly(oxypropylene) amine prepared as described in Example 8.

The base fuel employed in the above multicylinder engine tests contained no fuel detergent. The test compounds were admixed with the base fuel at the indicated concentrations.

The data in Table IV demonstrates that the combination of a polyalkylphenoxyalkyl aromatic ester and a poly (oxyalkylene) amine has a synergistic effect and gives significantly better intake valve deposit control than the aromatic ester component with a carrier fluid. Moreover, the data in Table IV further demonstrates that the combination of aromatic ester and poly(oxyalkylene) amine produces fewer combustion chamber deposits than the aromatic ester component with a carrier fluid.

What is claimed is:

1. A fuel additive composition comprising:
  (a) an aromatic ester compound of the formula:

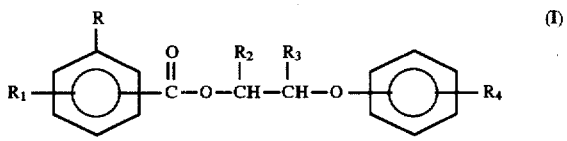

(I)

or a fuel soluble salt thereof, wherein R is hydroxy, nitro or —$(CH_2)_x$—$NR_5R_6$, wherein $R_5$ and $R_6$ are independently hydrogen or lower alkyl having 1 to 6 carbon atoms and x is 0 or 1;

$R_1$ is hydrogen, hydroxy, nitro or —$NR_7R_8$, wherein $R_7$ and $R_8$ are independently hydrogen or lower alkyl having 1 to 6 carbon atoms;

$R_2$ and $R_3$ are independently hydrogen or lower alkyl having 1 to 6 carbon atoms; and $R_4$ is a polyalkyl group having an average molecular weight in the range of about 450 to 5,000; and (b) a poly(oxyalkylene) amine having at least one basic nitrogen atom and a sufficient number of oxyalkylene units to render the poly(oxyalkylene) amine soluble in hydrocarbons boiling in the gasoline or diesel fuel range.

2. The fuel additive composition according to claim 1, wherein R is nitro, amino or —$CH_2NH_2$.

3. The fuel additive composition according to claim 2, wherein R is amino, or —$CH_2NH_2$.

4. The fuel additive composition according to claim 3, wherein R is amino.

5. The fuel additive composition according to claim 1, wherein $R_1$ is hydrogen, hydroxy, nitro or amino.

6. The fuel additive composition according to claim 5, wherein $R_1$ is hydrogen or hydroxy.

7. The fuel additive composition according to claim 6, wherein $R_1$ is hydrogen.

8. The fuel additive composition according to claim 1, wherein one of $R_2$ and $R_3$ is hydrogen or lower alkyl of 1 to 4 carbon atoms, and the other is hydrogen.

9. The fuel additive composition according to claim 8, wherein one of $R_2$ and $R_3$ is hydrogen, methyl or ethyl, and the other is hydrogen.

10. The fuel additive composition according to claim 9, wherein $R_2$ is hydrogen, methyl or ethyl, and $R_3$ is hydrogen.

11. The fuel additive composition according to claim 1, wherein $R_4$ is a polyalkyl group having an average molecular weight in the range of about 500 to 3,000.

12. The fuel additive composition according to claim 11, wherein $R_4$ is a polyalkyl group having an average molecular weight in the range of about 700 to 3,000.

13. The fuel additive composition according to claim 12, wherein $R_4$ is a polyalkyl group having an average molecular weight in the range of about 900 to 2,500.

14. The fuel additive composition according to claim 1, wherein $R_4$ is a polyalkyl group derived from polypropylene, polybutene, or a polyalphaolefin oligomer of 1-octene or 1-decene.

15. The fuel additive composition according to claim 14, wherein $R_4$ is a polyalkyl group derived from polyisobutene.

16. The fuel additive composition according to claim 15, wherein the polyisobutene contains at least about 20% of a methylvinylidene isomer.

17. The fuel additive composition according to claim 1, wherein R is amino, $R_1$, $R_2$ and $R_3$ are hydrogen and $R_4$ is a polyalkyl group derived from polyisobutene.

18. The fuel additive composition according to claim 1, wherein said poly(oxyalkylene) amine has a molecular weight in the range of about 500 to about 10,000.

19. The fuel additive composition according to claim 1, wherein said poly(oxyalkylene) amine contains at least about 5 oxyalkylene units.

20. The fuel additive composition according to claim 1, wherein said poly(oxyalkylene) amine is a hydrocarbyl poly(oxyalkylene) polyamine.

21. The fuel additive composition according to claim 1, wherein said poly(oxyalkylene) amine is a hydrocarbyl poly(oxyalkylene) aminocarbamate.

22. The fuel additive composition according to claim 21, wherein the hydrocarbyl group of said hydrocarbyl poly(oxyalkylene) aminocarbamate contains from 1 to about 30 carbon atoms.

23. The fuel additive composition according to claim 22, wherein said hydrocarbyl group of said hydrocarbyl poly(oxyalkylene) aminocarbamate is an alkylphenyl group.

24. The fuel additive composition according to claim 23, wherein the alkyl moiety of said alkylphenyl group is tetrapropenyl.

25. The fuel additive composition according to claim 21, wherein the amine moiety of said hydrocarbyl poly(oxyalkylene) aminocarbamate is derived from a polyamine having from 2 to 12 amine nitrogen atoms and from 2 to 40 carbon atoms.

26. The fuel additive composition according to claim 25, wherein said polyamine is a polyalkylene polyamine having 2 to 12 amine nitrogen atoms and 2 to 24 carbon atoms.

27. The fuel additive composition according to claim 26, wherein said polyalkylene polyamine is selected from the group consisting of ethylenediamine, propylenediamine, diethylenetriamine and dipropylenetriamine.

28. The fuel additive composition according to claim 21, wherein the poly(oxyalkylene) moiety of said hydrocarbyl poly(oxyalkylene) aminocarbamate is derived from $C_2$ to $C_5$ oxyalkylene units.

29. The fuel additive composition according to claim 21, wherein said hydrocarbyl poly(oxyalkylene) aminocarbamate is an alkylphenyl poly(oxybutylene) aminocarbamate, wherein the amine moiety is derived from ethylenediamine or diethylenetriamine.

30. The fuel additive composition according to claim 1, wherein said poly(oxyalkylene) amine is a hydrocarbyl poly(oxyalkylene) monoamine.

31. The fuel additive composition according to claim 30, wherein said hydrocarbyl poly(oxyalkylene) monoamine is an alkylphenyl poly(oxyalkylene) monoamine, wherein the poly(oxyalkylene) moiety contains oxypropylene units or oxybutylene units or mixtures thereof.

32. The fuel additive composition according to claim 31, wherein the alkylphenyl group is tetrapropenylphenyl.

33. A fuel composition comprising a major amount of hydrocarbons boiling in the gasoline or diesel range and an effective deposit-controlling amount of a fuel additive composition comprising:

(a) an aromatic ester compound of the formula:

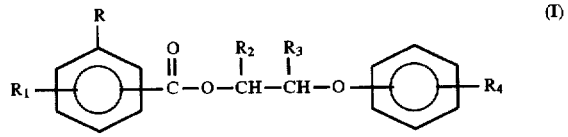

(I)

or a fuel soluble salt thereof, wherein R is hydroxy, nitro or —$(CH_2)_x$—$NR_5R_6$, wherein $R_5$ and $R_6$ are independently hydrogen or lower alkyl having 1 to 6 carbon atoms and x is 0 or 1;

$R_1$ is hydrogen, hydroxy, nitro or —$NR_7R_8$, wherein $R_7$ and $R_8$ are independently hydrogen or lower alkyl having 1 to 6 carbon atoms;

$R_2$ and $R_3$ are independently hydrogen or lower alkyl having 1 to 6 carbon atoms; and $R_4$ is a polyalkyl group having an average molecular weight in the range of about 450 to 5,000; and (b) a poly(oxyalkylene) amine having at least one basic nitrogen atom and a sufficient number of oxyalkylene units to render the poly(oxyalkylene) amine soluble in hydrocarbons boiling in the gasoline or diesel fuel range.

34. The fuel composition according to claim 33, wherein R is nitro, amino or —$CH_2NH_2$.

35. The fuel composition according to claim 34, wherein R is amino, or —$CH_2NH_2$.

36. The fuel composition according to claim 35, wherein R is amino.

37. The fuel composition according to claim 33, wherein $R_1$ is hydrogen, hydroxy, nitro or amino.

38. The fuel composition according to claim 37, wherein $R_1$ is hydrogen or hydroxy.

39. The fuel composition according to claim 38, wherein R₁ is hydrogen.

40. The fuel composition according to claim 33, wherein one of R₂ and R₃ is hydrogen or lower alkyl of 1 to 4 carbon atoms, and the other is hydrogen.

41. The fuel composition according to claim 40, wherein one of R₂ and R₃ is hydrogen, methyl or ethyl, and the other is hydrogen.

42. The fuel composition according to claim 41, wherein R₂ is hydrogen, methyl or ethyl, and R₃ is hydrogen.

43. The fuel composition according to claim 33, wherein R₄ is a polyalkyl group having an average molecular weight in the range of about 500 to 3,000.

44. The fuel composition according to claim 43, wherein R₄ is a polyalkyl group having an average molecular weight in the range of about 700 to 3,000.

45. The fuel composition according to claim 44, wherein R₄ is a polyalkyl group having an average molecular weight in the range of about 900 to 2,500.

46. The fuel composition according to claim 33, wherein R₄ is a polyalkyl group derived from polypropylene, polybutene, or a polyalphaolefin oligomer of 1-octene or 1-decene.

47. The fuel composition according to claim 46, wherein R₄ is a polyalkyl group derived from polyisobutene.

48. The fuel composition according to claim 47, wherein the polyisobutene contains at least about 20% of a methylvinylidene isomer.

49. The fuel composition according to claim 33, wherein R is amino, R₁, R₂ and R₃ are hydrogen and R₄ is a polyalkyl group derived from polyisobutene.

50. The fuel composition according to claim 33, wherein the composition contains from about 25 to about 2,000 parts per million by weight of said aromatic ester compound and about 25 to about 2,000 parts per million of said poly (oxyalkylene) amine.

51. The fuel composition according to claim 33, where the composition further contains from about 25 to about 5,000 parts per million by weight of a fuel-soluble, nonvolatile carrier fluid.

52. The fuel composition according to claim 33, wherein said poly(oxyalkylene) amine is a hydrocarbyl poly (oxyalkylene) aminocarbamate.

53. The fuel composition according to claim 52, wherein the hydrocarbyl group of said hydrocarbyl poly (oxyalkylene) aminocarbamate contains from 1 to about 30 carbon atoms; and wherein the amine moiety of said hydrocarbyl poly(oxyalkylene) aminocarbamate is derived from a polyamine having from 2 to 12 amine nitrogen atoms and from 2 to 40 carbon atoms.

54. The fuel composition according to claim 53, wherein said hydrocarbyl group of said hydrocarbyl poly (oxyalkylene) aminocarbamate is an alkylphenyl group; and wherein said polyalkylene polyamine is selected from the group consisting of ethylenediamine, propylenediamine, diethylenetriamine and dipropylenetriamine.

55. The fuel composition according to claim 54, wherein the alkyl moiety of said alkylphenyl group is tetrapropenyl.

56. The fuel composition according to claim 52, wherein said hydrocarbyl poly(oxyalkylene) aminocarbamate is an alkylphenyl poly(oxybutylene) aminocarbamate, wherein the amine moiety is derived from ethylenediamine or diethylenetriamine.

57. The fuel composition according to claim 33, wherein said poly(oxyalkylene) amine is a hydrocarbyl poly (oxyalkylene) monoamine.

58. The fuel composition according to claim 57, wherein said hydrocarbyl poly(oxyalkylene) monoamine is an alkylphenyl poly(oxyalkylene) monoamine, wherein the poly (oxyalkylene) moiety contains oxypropylene units or oxybutylene units or mixtures thereof.

59. The fuel composition according to claim 58, wherein the alkylphenyl group is tetrapropenylphenyl.

60. A fuel concentrate comprising an inert stable oleophilic organic solvent boiling in the range of from about 150° F. to 400° F. and from about 10 to about 70 weight percent of a fuel additive composition comprising:

(a) an aromatic ester compound of the formula:

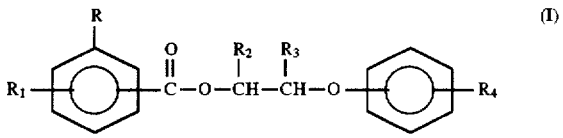

or a fuel soluble salt thereof, wherein R is hydroxy, nitro or —(CH₂)ₓ—NR₅R₆, wherein R₅ and R₆ are independently hydrogen or lower alkyl having 1 to 6 carbon atoms and x is 0 or 1;

R₁ is hydrogen, hydroxy, nitro or —NR₇R₈, wherein R₇ and R₈ are independently hydrogen or lower alkyl having 1 to 6 carbon atoms;

R₂ and R₃ are independently hydrogen or lower alkyl having 1 to 6 carbon atoms; and R₄ is a polyalkyl group having an average molecular weight in the range of about 450 to 5,000; and (b) a poly (oxyalkylene) amine having at least one basic nitrogen atom and a sufficient number of oxyalkylene units to render the poly(oxyalkylene) amine soluble in hydrocarbons boiling in the gasoline or diesel fuel range.

61. The fuel concentrate according to claim 60, wherein R is nitro, amino or —CH₂NH₂.

62. The fuel concentrate according to claim 61, wherein R is amino, or —CH₂NH₂.

63. The fuel concentrate according to claim 62, wherein R is amino.

64. The fuel concentrate according to claim 60, wherein R₁ is hydrogen, hydroxy, nitro or amino.

65. The fuel concentrate according to claim 64, wherein R₁ is hydrogen or hydroxy.

66. The fuel concentrate according to claim 65, wherein R₁ is hydrogen.

67. The fuel concentrate according to claim 60, wherein one of R₂ and R₃ is hydrogen or lower alkyl of 1 to 4 carbon atoms, and the other is hydrogen.

68. The fuel concentrate according to claim 67, wherein one of R₂ and R₃ is hydrogen, methyl or ethyl, and the other is hydrogen.

69. The fuel concentrate according to claim 68, wherein R₂ is hydrogen, methyl or ethyl, and R₃ is hydrogen.

70. The fuel concentrate according to claim 60, wherein R₄ is a polyalkyl group having an average molecular weight in the range of about 500 to 3,000.

71. The fuel concentrate according to claim 70, wherein R₄ is a polyalkyl group having an average molecular weight in the range of about 700 to 3,000.

72. The fuel concentrate according to claim 71, wherein R₄ is a polyalkyl group having an average molecular weight in the range of about 900 to 2,500.

73. The fuel concentrate according to claim 60, wherein R₄ is a polyalkyl group derived from polypropylene, polybutene, or a polyalphaolefin oligomer of 1-octene or 1-decene.

74. The fuel concentrate according to claim 73, wherein R₄ is a polyalkyl group derived from polyisobutene.

75. The fuel concentrate according to claim 74, wherein the polyisobutene contains at least about 20% of a methylvinylidene isomer.

76. The fuel concentrate according to claim 60, wherein R is amino, $R_1$, $R_2$ and $R_3$ are hydrogen and $R_4$ is a polyalkyl group derived from polyisobutene.

77. The fuel concentrate according to claim 60, wherein the fuel concentrate further contains from about 20 to about 60 weight percent of a fuel-soluble, nonvolatile carrier fluid.

78. The fuel concentrate according to claim 60, wherein said poly(oxyalkylene) amine is a hydrocarbyl poly(oxyalkylene) aminocarbamate.

79. The fuel concentrate according to claim 78, wherein the hydrocarbyl group of said hydrocarbyl poly(oxyalkylene) aminocarbamate contains from 1 to about 30 carbon atoms; and wherein the amine moiety of said hydrocarbyl poly(oxyalkylene) aminocarbamate is derived from a polyamine having from 2 to 12 amine nitrogen atoms and from 2 to 40 carbon atoms.

80. The fuel concentrate according to claim 79, wherein said hydrocarbyl group of said hydrocarbyl poly(oxyalkylene) aminocarbamate is an alkylphenyl group; and wherein said polyalkylene polyamine is selected from the group consisting of ethylenediamine, propylenediamine, diethylenetriamine and dipropylenetriamine.

81. The fuel concentrate according to claim 80, wherein the alkyl moiety of said alkylphenyl group is tetrapropenyl.

82. The fuel concentrate according to claim 78, wherein said hydrocarbyl poly(oxyalkylene) aminocarbamate is an alkylphenyl poly(oxybutylene) aminocarbamate, wherein the amine moiety is derived from ethylenediamine or diethylenetriamine.

83. The fuel concentrate according to claim 60, wherein said poly(oxyalkylene) amine is a hydrocarbyl poly(oxyalkylene) monoamine.

84. The fuel concentrate according to claim 83, wherein said hydrocarbyl poly(oxyalkylene) monoamine is an alkylphenyl poly(oxyalkylene) monoamine, wherein the poly(oxyalkylene) moiety contains oxypropylene units or oxybutylene units or mixtures thereof.

85. The fuel concentrate according to claim 84, wherein the alkylphenyl group is tetrapropenylphenyl.

* * * * *